(12) United States Patent
    Solie

(10) Patent No.: US 12,603,174 B2
(45) Date of Patent: *Apr. 14, 2026

(54) METHOD FOR UTILIZING A MEDICAL SERVICES KIOSK

(71) Applicant: OnMed LLC, Tampa, FL (US)

(72) Inventor: Leonard Solie, Tampa, FL (US)

(73) Assignee: OnMed LLC, White Plains, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/798,525

(22) Filed: Aug. 8, 2024

(65) Prior Publication Data

US 2024/0404697 A1     Dec. 5, 2024

Related U.S. Application Data

(63) Continuation of application No. 16/692,934, filed on Nov. 22, 2019, now Pat. No. 12,119,112, which is a
(Continued)

(51) Int. Cl.
    *G16H 80/00*       (2018.01)
    *A61B 5/00*        (2006.01)
    (Continued)

(52) U.S. Cl.
    CPC ........... *G16H 40/67* (2018.01); *A61B 5/0077* (2013.01); *A61B 5/6888* (2013.01); *A61B 5/742* (2013.01);
    (Continued)

(58) Field of Classification Search
    None
    See application file for complete search history.

(56) References Cited

U.S. PATENT DOCUMENTS

| | | | |
|---|---|---|---|
| D97,516 S | 11/1935 | Ward | |
| 2,707,426 A | 5/1955 | Cooper | |

(Continued)

FOREIGN PATENT DOCUMENTS

| | | |
|---|---|---|
| EP | 2940612 A1 | 11/2015 |
| JP | 2010004525 A | 1/2010 |

(Continued)

OTHER PUBLICATIONS

Screen shot of Internet web site http://bigthink.com—Teaches virtual doctor in a kiosk Link: http://bigthink.com/ideas/40455?page=aii.

(Continued)

*Primary Examiner* — Robert A Sorey
(74) *Attorney, Agent, or Firm* — Darrow Mustafa, PC

(57)     ABSTRACT

A medical services kiosk supporting private and secure telemedicine sessions between a patient and a remote network terminal utilized by a remote health care professional. The medical services kiosk comprising at least one privacy chamber having at least one door and at least one window. Each privacy chamber may include a user interactive display terminal that includes a display device, an input device, and a centralized processor, wherein the centralized processor is electronically communicable with the remote network terminal and a cloud based system. Each patient station may each include at least one documentation receiving device, at least one biometric device for obtaining biometric health measurements of the patient utilizing the at least one patient station, an arm mechanism, a seating mechanism, a camera, a retractable diagnostic camera device, a lighting mechanism that lights the privacy chamber, and a purification system.

20 Claims, 12 Drawing Sheets

Related U.S. Application Data continuation of application No. 16/573,756, filed on Sep. 17, 2019, now Pat. No. 11,978,552, which is a continuation-in-part of application No. 16/275,741, filed on Feb. 14, 2019, now Pat. No. 12,322,517, which is a continuation-in-part of application No. 13/777,864, filed on Feb. 26, 2013, now abandoned.

(60) Provisional application No. 61/606,095, filed on Mar. 2, 2012.

(51) Int. Cl.

| | |
|---|---|
| *G16H 10/60* | (2018.01) |
| *G16H 40/67* | (2018.01) |
| *A61L 9/20* | (2006.01) |
| *B65D 83/00* | (2006.01) |
| *G06F 21/62* | (2013.01) |
| *G06Q 20/22* | (2012.01) |

(52) U.S. Cl.

CPC ............ *G16H 10/60* (2018.01); *G16H 80/00* (2018.01); *A61B 5/0022* (2013.01); *A61L 9/20* (2013.01); *B65D 83/00* (2013.01); *G06F 21/6245* (2013.01); *G06Q 20/22* (2013.01)

(56) References Cited

U.S. PATENT DOCUMENTS

| | | | |
|---|---|---|---|
| D254,751 S | | 4/1980 | Adler et al. |
| 5,024,650 A | | 6/1991 | Hagiwara et al. |
| 5,255,682 A | | 10/1993 | Pawluskiewicz et al. |
| D355,716 S | | 2/1995 | Nash et al. |
| 5,486,109 A | | 1/1996 | Hunter et al. |
| D390,666 S | | 2/1998 | Lagerlof |
| 5,773,767 A | | 6/1998 | Collins, Jr |
| D412,035 S | | 7/1999 | Kleihues |
| 5,924,206 A | | 7/1999 | Cote et al. |
| 6,046,761 A | | 4/2000 | Echerer |
| 6,190,367 B1 | | 2/2001 | Hall |
| 6,205,716 B1 | * | 3/2001 | Peltz ..................... H04N 7/142 |
| | | | 379/453 |
| D445,914 S | | 7/2001 | Helminiak |
| 6,428,124 B1 | | 8/2002 | Bluth et al. |
| D484,131 S | | 12/2003 | Olson et al. |
| D501,557 S | | 2/2005 | Collins et al. |
| 6,941,285 B2 | | 9/2005 | Sarcanin |
| 7,100,820 B2 | | 9/2006 | Michelassi et al. |
| D549,352 S | | 8/2007 | Singh |
| 7,318,050 B1 | | 1/2008 | Musgrave |
| 7,337,950 B2 | | 3/2008 | Devault |
| 7,347,362 B2 | | 3/2008 | Michelassi et al. |
| 7,445,600 B1 | | 11/2008 | Carr et al. |
| 7,494,048 B2 | | 2/2009 | Gusler et al. |
| D595,425 S | | 6/2009 | Jackson et al. |
| 7,699,220 B2 | | 4/2010 | Barcelou |
| 7,857,207 B1 | | 12/2010 | Hopkins, III |
| 7,912,733 B2 | | 3/2011 | Clements et al. |
| 7,986,369 B1 | | 7/2011 | Burns |
| 8,025,213 B2 | | 9/2011 | Hartfield et al. |
| 8,118,222 B2 | | 2/2012 | Barcelou |
| 8,130,111 B2 | | 3/2012 | Crowley et al. |
| D658,295 S | | 4/2012 | Geijsen et al. |
| D695,410 S | | 12/2013 | Becker |
| D712,539 S | | 9/2014 | Hansen et al. |
| D726,333 S | | 4/2015 | Bogan |
| D735,343 S | | 7/2015 | Dorsey et al. |
| D735,868 S | | 8/2015 | Mareguddi et al. |
| 9,179,051 B1 | | 11/2015 | Stoudt |
| D745,188 S | | 12/2015 | Hart |
| 9,208,287 B2 | * | 12/2015 | Waterson .............. G16H 50/20 |
| D746,925 S | | 1/2016 | Firth et al. |
| 9,261,262 B1 | | 2/2016 | Baloga |
| 9,449,148 B2 | | 9/2016 | Holmes |
| D783,604 S | | 4/2017 | Wesolek |
| D791,967 S | | 7/2017 | Goldberg |
| 9,723,273 B2 | | 8/2017 | Child |
| D796,693 S | | 9/2017 | Mount |
| 9,763,271 B1 | | 9/2017 | Gabel |
| D804,671 S | | 12/2017 | Yanase et al. |
| 10,233,659 B1 | | 3/2019 | Holdredge et al. |
| D854,188 S | | 7/2019 | Schaeken et al. |
| D859,634 S | | 9/2019 | Hochman et al. |
| 2002/0133544 A1 | | 9/2002 | Aoike et al. |
| 2002/0172631 A1 | | 11/2002 | Chandler |
| 2003/0178233 A1 | | 9/2003 | Montagnino et al. |
| 2003/0216831 A1 | | 11/2003 | Hart |
| 2003/0233129 A1 | | 12/2003 | Matos |
| 2004/0044560 A1 | | 3/2004 | Giglio et al. |
| 2004/0122713 A1 | | 6/2004 | Hill, Sr. et al. |
| 2004/0145676 A1 | | 7/2004 | Lin |
| 2005/0075907 A1 | | 4/2005 | Rao |
| 2005/0229834 A1 | | 10/2005 | Wong |
| 2005/0241026 A1 | | 10/2005 | Esler et al. |
| 2005/0288571 A1 | | 12/2005 | Perkins et al. |
| 2006/0028717 A1 | | 2/2006 | Dunn |
| 2006/0095297 A1 | | 5/2006 | Virik |
| 2006/0106646 A1 | | 5/2006 | Squilla et al. |
| 2006/0122470 A1 | | 6/2006 | Schulz |
| 2006/0143041 A1 | | 6/2006 | Tipirneni |
| 2006/0143997 A1 | | 7/2006 | Libenson |
| 2006/0155589 A1 | | 7/2006 | Lane |
| 2006/0173267 A1 | | 8/2006 | Chiang et al. |
| 2006/0271400 A1 | | 11/2006 | Clements et al. |
| 2006/0290885 A1 | | 12/2006 | Covannon et al. |
| 2007/0073113 A1 | | 3/2007 | Squilla et al. |
| 2007/0129610 A1 | | 6/2007 | Squilla |
| 2007/0208241 A1 | | 9/2007 | Drucker |
| 2007/0288265 A1 | | 12/2007 | Quinian |
| 2008/0139947 A1 | | 6/2008 | O'Hanlon et al. |
| 2008/0191008 A1 | | 8/2008 | Manfredi et al. |
| 2009/0089085 A1 | | 4/2009 | Schoenberg |
| 2009/0137047 A1 | | 5/2009 | Regan et al. |
| 2009/0137882 A1 | | 5/2009 | Baudino et al. |
| 2009/0160876 A1 | | 6/2009 | King et al. |
| 2009/0167531 A1 | | 7/2009 | Ferguson |
| 2009/0167838 A1 | | 7/2009 | Poisner |
| 2009/0240527 A1 | | 9/2009 | Bluth |
| 2009/0240528 A1 | | 9/2009 | Bluth |
| 2009/0241177 A1 | | 9/2009 | Bluth |
| 2009/0307989 A1 | | 12/2009 | Johnson, Jr. |
| 2010/0023538 A1 | | 1/2010 | Kreiner et al. |
| 2010/0130873 A1 | | 5/2010 | Yuen |
| 2010/0186162 A1 | | 7/2010 | Leonard |
| 2010/0222649 A1 | | 9/2010 | Schoenberg |
| 2010/0286492 A1 | | 11/2010 | Baudino et al. |
| 2011/0014955 A1 | | 1/2011 | Kim |
| 2011/0114744 A1 | | 5/2011 | Ricciardi et al. |
| 2011/0122995 A1 | | 5/2011 | Ferro, Jr. |
| 2011/0130635 A1 | | 6/2011 | Ross |
| 2011/0161100 A1 | | 6/2011 | Peak |
| 2011/0186627 A1 | | 8/2011 | Kreamer |
| 2011/0191123 A1 | | 8/2011 | Buzynski |
| 2011/0248818 A1 | | 10/2011 | Hashim-Waris |
| 2011/0307265 A1 | | 12/2011 | Bannis |
| 2011/0315611 A1 | | 12/2011 | Fulkerson |
| 2012/0061338 A1 | | 3/2012 | Willick et al. |
| 2012/0275167 A1 | | 11/2012 | Scruggs et al. |
| 2012/0284512 A1 | | 11/2012 | Agarwal et al. |
| 2012/0289850 A1 | | 11/2012 | Xu |
| 2013/0000218 A1 | | 1/2013 | Uffner et al. |
| 2013/0014985 A1 | | 1/2013 | Ferrara |
| 2013/0062127 A1 | | 3/2013 | Pangrazio |
| 2013/0173287 A1 | | 7/2013 | Cashman et al. |
| 2013/0186429 A1 | | 7/2013 | Morita |
| 2013/0246084 A1 | | 9/2013 | Parmanto et al. |
| 2013/0314852 A1 | | 11/2013 | Kincaid et al. |
| 2014/0052463 A1 | | 2/2014 | Cashman et al. |
| 2014/0081656 A1 | | 3/2014 | Alamri |
| 2014/0095196 A1 | | 4/2014 | Waterson et al. |
| 2014/0139616 A1 | | 5/2014 | Pinter et al. |
| 2014/0251401 A1 | | 9/2014 | Barber |
| 2014/0330579 A1 | | 11/2014 | Cashman et al. |
| 2015/0248536 A1 | | 9/2015 | Tawil |

(56) References Cited

U.S. PATENT DOCUMENTS

| | | | |
|---|---|---|---|
| 2016/0085935 A1 | 3/2016 | Waterson et al. | |
| 2016/0105641 A1 | 4/2016 | Periyannan et al. | |
| 2017/0032092 A1 | 2/2017 | Mink et al. | |
| 2017/0186712 A1 | 6/2017 | Shen et al. | |
| 2017/0323070 A1 | 11/2017 | Hodge | |
| 2017/0374502 A1 | 12/2017 | Gabel | |
| 2018/0110475 A1 | 4/2018 | Shaya | |
| 2020/0027568 A1 | 1/2020 | Foshee, Jr. et al. | |
| 2020/0069827 A1* | 3/2020 | Mangiardi | A47L 11/282 |
| 2020/0070214 A1* | 3/2020 | Mangiardi | F21S 10/02 |
| 2020/0078125 A1* | 3/2020 | Mangiardi | A61G 13/12 |
| 2020/0242575 A1 | 7/2020 | Shell et al. | |
| 2021/0035400 A1 | 2/2021 | Flynn et al. | |

FOREIGN PATENT DOCUMENTS

| | | | | |
|---|---|---|---|---|
| WO | 2002096339 A1 | 12/2002 | | |
| WO | 2011011909 A1 | 2/2011 | | |
| WO | 2014002091 A2 | 1/2014 | | |
| WO | WO-2018087171 A1 * | 5/2018 | | F21V 33/0072 |

OTHER PUBLICATIONS

Screen shot of Internet web site www.emrandellr.com—Teaches virtual doctor in a kiosk Link: http://www.ernrandehr.corn/2011 /1 0/03/vi rtual-doc-kiosks-a-g iant-ieap-f or-telehealth/.

Screen shot of Internet web site www<fastcompany.com http:i/www.fastcompany.com/rnagazine/155/H1e-virtual-doctor-wiil-see-you-now.htrnl.

Screen shot of Internet web site www.rnedlegalsource.com—teaches a combined medicalilegal consulting website Link: I1ttp://www. med legalsou rce. com/terms-of-use.

U.S. Appl. No. 16/692,934, filed Nov. 22, 2019, issued as U.S. Pat. No. 12,119,112.

U.S. Appl. No. 16/573,756, filed Sep. 17, 2019, issued as U.S. Pat. No. 11,978,552.

U.S. Appl. No. 16/275,741, filed Feb. 14, 2019, now allowed.

U.S. Appl. No. 13/777,864, filed Feb. 26, 2013, now abandoned.

Lu et al. "Transforming telemedicine for rural and urban communities Telemedicine 2.0—any doctor, any place, any time," The 12th IEEE International Conference one-Health Networking, Applications and Services, Lyon, France, 2010, pp. 379-385 (7 pages).

Ramachandran, "Virtual Doc Kiosks—a giant leap for telehealth," Healthcare IT Today, Fresh, Daily, Practical Healthcare IT Insights, Oct. 3, 2011, https://www.emrandehr.com/2011/10/03/virtual-doc-kiosks-a-giant-leap-for-telehealth/ (4 pages).

Silva, "Ideas Are Immortal," Jun. 27, 2013, found at https://bigthink.com/articles/ideas-are-immortal/ (5 pages).

Svoboda, "Cisco's Virtual Doctor Will See You Now," Apr. 20, 2011, found at https://www.fastcompany.com/1747588/ciscos-virtual-doctor-will-see-you-now (8 pages).

https://web.archive.org/web/20190509133902/https://onmed.com/ (33 pages).

https://www.medlegalsource.com/terms-of-use.

* cited by examiner

METHOD FOR UTILIZING A MEDICAL SERVICES KIOSK

CROSS-REFERENCE TO RELATED APPLICATIONS

This U.S. nonprovisional patent application is a continuation application of U.S. nonprovisional patent application Ser. No. 16/573,756, filed on Sep. 17, 2019, which claims the benefit of U.S. nonprovisional patent application Ser. No. 16/275,741, filed on Feb. 14, 2019, which claims the benefit of U.S. nonprovisional patent application Ser. No. 13/777,864, filed on Feb. 26, 2013, which, in-turn, claims the benefit of U.S. provisional patent application Ser. No. 61/606,095, filed on Mar. 2, 2012, all-of-which are incorporated-by-reference herein in their entirety.

FIELD OF THE INVENTION

The present invention relates generally to a medical kiosk, and more particularly, to a medical kiosk or booth that includes a plurality of medical equipment that allows a patient to perform basic physical examinations during a medical session through the help and guidance of a physician who is remotely connected supervising the medical session.

BACKGROUND OF THE INVENTION

Medical care is a need for every individual and every family. Many individuals have one or more physicians or other medical professionals that they see for wellness visits and for treatment of various illnesses and injuries. However, as the population continues to grow and healthcare continues to evolve, the need for doctors and health care providers continues to grow as well. As a result of this growth, medical facilities such as hospitals and doctors' offices are operating at maximum physical capacity. Since the population continues to grow and the need for doctors and health care providers is not expected to abate in the near or immediate future, there is a need for an alternative more efficient manner to see patients rather than physically seeing them on-site.

Medical facilities in general have been attempting to improve efficiency through utilizing technology. In particular, some aspects of patient care have been computerized through the use of electronic terminals interactively accessible to the patients. Currently, processes such as checking in and prescription refill requests may be handled entirely by digital mediums. These digital mediums may be in the form of specialized hardware and software for collecting, organizing, and updating information associated with patients.

Hospitals and medical clinics recently began utilizing interactive devices that allow patients to perform routine activities. The ability for patients to perform operations such as update personal information linked to their health profile, pay medical fees, and other various routine activities via these interactive devices has generated a significant increase in efficiency for medical facilities. However, patients are still required to be physically on-site in order for medical professionals to perform routine medical activities that are necessary to treat a patient such as measuring vital signs.

There have also been limitations regarding doctor and medical professional availability in the case when an individual requires immediate attention. For example, if an individual were to decide to visit a doctor or medical professional's office for a non-emergency the day of, then that individual would be classified as a "walk-in" if he or she did not have an appointment and would be subjected to a wait time associated with the current workload of the medical facility. The individual's only alternative would be to go to the emergency room of a hospital for a non-emergency matter.

Recently, there have been developments in implementations of various systems and methods relating to telehealth and telemedicine. However, these systems and methods require a substantial amount of improvement in order for them to be nearly as efficient as the conventional practice of medicine.

Thus, there is a need for a medical services system that allows doctors and other medical professionals to examine, diagnose, and treat patients without requiring the patients to be physically present with the medical professional.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY OF THE INVENTION

The present invention is directed to a medical services kiosk that is capable of generating a plurality of interactions between a user or patient and one or more medical professionals via a network comprising a plurality of client devices. The medical services kiosk further comprises a patient station that satisfies the need for providing facilities for remote interaction with health care professionals in real time. The medical services kiosk is configured to support examination, diagnosis, and treatment of a patient via establishing a tele-communicative connection between the patient and remote medical professionals via the network.

Introducing a first embodiment of the invention a medical services kiosk, comprising:

a unit defining an interior space having a closed top, a closed bottom, a pair of opposite right and left sides, a front end, and a back end;

at least one patient station provided inside of the interior space of the unit, the at least one patient station comprising:

a privacy chamber having at least one door, wherein the privacy chamber is provided for receiving a patient therein and permitting the patient to communicate over a network with a remote health care professional;

an electronic device, wherein the electronic device is electronically communicable over the network with a remotely located network terminal accessible by the remote health care professional;

at least one documentation receiving device;

at least one biometric device for obtaining biometric health measurements of the patient utilizing the at least one patient station;

a camera configured to transmit a real-time image of the patient to said remotely located network terminal accessible by the remote health care professional over the network;

a retractable diagnostic camera;

a lighting mechanism that lights said privacy chamber; and a purification system, wherein the at least one documentation receiving device, the at least one biometric device, the camera, and the retractable diagnostic camera are communicable with the electronic device.

In another aspect, the at least one patient station may further comprise a privacy system that includes an electronic lock coupled to the at least one door, and a privacy feature applicable to a glass window provided by the at least one door.

In yet another aspect, the privacy system may be communicative with the at least one documentation receiving device and said user interactive display terminal, wherein said privacy system is configured to activate when the patient initiates a session with the health care professional.

In another aspect, the at least one documentation device may include a card reader. The card reader may be capable of accepting at least one of the group of credit cards, gift cards, and insurance cards, for payment to initiate a session.

In another aspect, the display of the electronic device may be able to display a real-time image of the health care professional communicating with the patient when the session has started.

In yet another aspect, the patient station may further comprise an arm mechanism, the arm mechanism comprising: an arm rest, a support arm, and a wall mount. The arm rest and the support arm are hingeably attachable to the wall mount. The wall mount may be affixable to a wall surface provided by the privacy chamber. The arm rest may be configured to pivot about said hingeable attachment and movable between an upward position and a downward position.

In another aspect, the retractable diagnostic camera device, the lighting mechanism, and the sanitation system may be disposed about a false ceiling provided by the privacy chamber.

In yet another aspect, the retractable diagnostic camera device may comprise, a specialized camera head, an extendible cord attached to said specialized camera head, and a self-recoiling mechanism.

In another aspect, the retractable diagnostic camera device may be communicative with the electronic device that is electronically communicable with the remote network terminal accessed by the health care professional to provide the health care professional with real-time images and measurement readings of the patient.

In yet another aspect, the patient station may include a sanitation system that includes an ultra violet light device that is configured to activate when the privacy chamber is vacant for long periods of time, and when the patient has terminated the medical session with the healthcare professional and has left the privacy chamber.

In another aspect, the patient station may further comprise a medication inventory storage space having a medical dispenser. The medical dispenser may be communicative with the remote network terminal accessible by the health care professional, and controllable by the health care professional, such that the health care professional can selectively dispense a medication to the patient during an active session.

In another aspect, the patient station may further comprise a weight scale mechanism. The scale mechanism may be integrated to the flooring of the privacy chamber, and suitable and calibrated for obtaining an accurate reading of the patient's weight.

In yet another aspect, the patient station may further comprise a seating mechanism, the seating mechanism comprising: a seat rest, a seat support, and a wall mount.

In yet another aspect, the patient station may further comprise a back-up generator that energizes the station in the event of a power loss.

In yet another aspect, the patient station may further comprise at least one uninterruptible power supply (UPS) battery supply that energizes the station in the event of a power loss.

In yet another aspect, the patient station may include antimicrobial surfaces.

Introducing a second embodiment of the invention of a medical services kiosk, comprising:

a unit defining an interior space having a closed top, a closed bottom, a pair of opposite right and left sides, a front end, and a back end;

at least two patient stations provided inside of said interior space adjacent one another and separated by at least one noise attenuation privacy wall, each of the patient stations, comprising:

a privacy chamber having at least one door and at least one window each having at least one panel comprising a transparency shifting mechanism and at least one locking mechanism, the transparency shifting mechanism and locking mechanism controlled by a privacy system that activates once a patient is received within the privacy chamber and commences a session with a remote network terminal utilized by a health care professional over a network connection;

an electronic device, wherein the electronic device is electronically communicable with the remote network terminal;

an electronic card reading device;

at least one biometric device for obtaining biometric health measurements of the patient;

a camera, said camera of each of the at least two patient stations configured to transmit a real-time image of the patient to the remotely located network terminal accessible by the health care professional over the network during the session;

a retractable diagnostic camera device, comprising;

a specialized camera head;

an extendible chord attached to said specialized camera head; and a self-recoiling mechanism adapted to receiving said extendable chord;

wherein the patient is able to grab and pull on said specialized camera head to perform a plurality of tasks as directed by the healthcare professional during said session, and wherein the diagnostic camera device is capable of communicating with the electronic device that is electronically communicative with the remote network terminal to provide said health care professional with real-time images and medical readings of the patient;

an arm mechanism selectively usable by the patient for arm stability when using the at least one biometric device;

a seating mechanism selectively useable when the patient communicates with the health care professional;

a sanitation device; and a lighting mechanism that lights said privacy chamber.

Introducing a method for providing remote real time patient ailment diagnoses and treatment, said method including the steps of:

receiving a patient within a patient station, said patient station comprising:

a privacy chamber having at least one door;
an electronic device, wherein said is electronically
   communicable over a network with a cloud based
   system and a remotely located network terminal;
at least one documentation receiving device;
a plurality of medical-related devices;
a retractable diagnostic camera;
a camera;
a seating mechanism;
an arm mechanism
a lighting mechanism that lights said privacy chamber;
a printer for printing a prescription;
a medicine dispenser; and
a purification system,
   wherein said at least one documentation receiving
      device, said plurality of medical-related devices,
      said retractable diagnostic camera, said camera,
      said printer, and said medicine dispenser are com-
      municable with said electronic device;
sending instructions from said electronic device to said
   cloud based system that said patient is initiating a
   medical session, wherein said medical session is facili-
   tated and hosted by said cloud based system
requiring said patient to provide medical insurance infor-
   mation readable by said at least one documentation
   device to establish said medical session;
activating a privacy system after said medical session has
   been initiated by said patient;
establishing a connection between said electronic device
   and said remotely located network terminal over said
   network, wherein said remotely located network termi-
   nal is accessible by a healthcare professional;
enabling bi-directional communication between said
   patient and said healthcare professional;
broadcasting a live image of said patient within said
   privacy chamber to said remotely located network
   terminal, said live image viewable by said healthcare
   professional;
broadcasting a live image of said healthcare professional
   overseeing said medical session to said electronic
   device, said live image viewable by said patient within
   said privacy chamber;
requesting said patient to select and use at least one
   medical-related device from said plurality of medical-
   related devices to run a medical diagnostic test;
transmitting readable data from said at least one of
   medical-related device used to perform said at least one
   medical diagnostic test by said patient to said remotely
   network terminal accessible by said healthcare profes-
   sional;
prescribing a medication;
determining by said electronic device if said medication
   prescribed is available in said medicine dispenser,
if, as a result of said determining step, said medication is
   available in said medicine dispenser, the step of dis-
   pensing said medication from said medicine dispenser;
   and
if, as a result of said determining step, said medication is
   instead not available in said medicine dispenser, the
   step of printing a medication prescription correspond-
   ing to said medication by way of said printer;
terminating said medical session;
deactivating said privacy system after said medical ses-
   sion has been terminated; and
purifying said privacy chamber by way of said purifica-
   tion system after said patient has left said privacy
   chamber.

6

As described herein, medical professional may include
but is not limited to any doctor, pharmacist, nurse practitio-
ner, nurse, nursing assistant, or any other individual who
examines and treats or assists in the examination and treat-
ment of patients for medical purposes.

These and other objects, features, and advantages of the
present invention will become more readily apparent from
the attached drawings and the detailed description of the
preferred embodiments, which follow.

BRIEF DESCRIPTION OF THE DRAWINGS

The preferred embodiments of the invention will herein-
after be described in conjunction with the appended draw-
ings provided to illustrate and not to limit the invention,
where like designations denote like elements, and in which:

FIG. 5 presents a cut-out view of the medical service
kiosk shown in FIG. 2, illustrating a few of the medical
equipment that the medical service kiosk is equipped with;

Like reference numerals refer to like parts throughout the
several views of the drawings.

DETAILED DESCRIPTION

In the following description, for the purposes of expla-
nation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
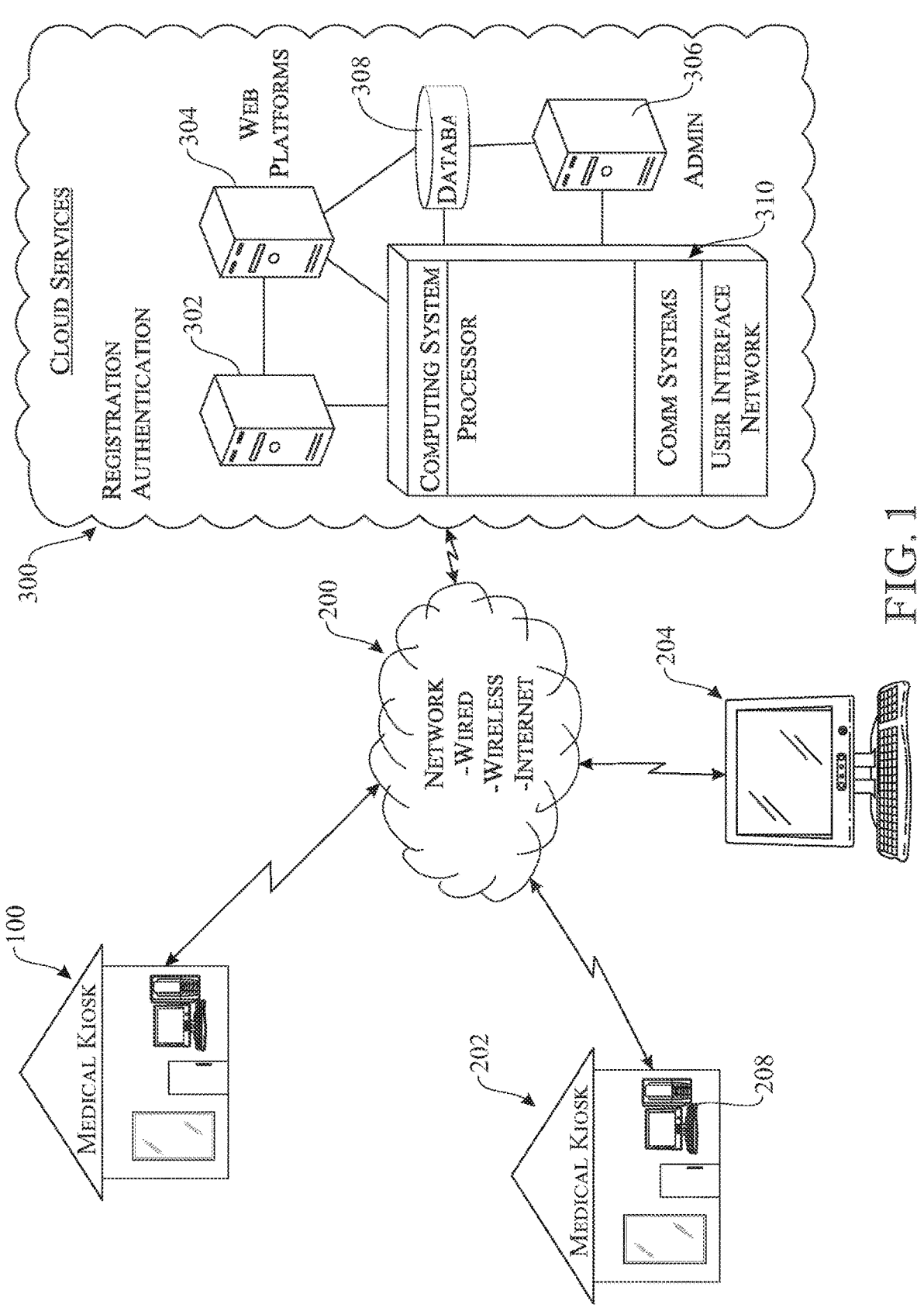
FIG. 1 presents a schematic view of a medical service
kiosk communicatively coupled to a medical facility located
remotely thereof, both the medical service kiosk and medi-
cal facility communicatively coupled to a cloud based server
via a network.

Initially referring to FIG. 1 there is shown a schematic view of a remote real time medical assistance system, showing a medical service kiosk 100, and a medical facility 202 in bidirectional communication and hosted on a cloud services system 300 over an accessible communication network 200, in accordance with an embodiment of the present invention. It is appreciated that any number of medical service kiosks 100 and medical facilities 202, which can include one or more terminals, computers or servers, can access and use the cloud services system 300. As illustrated in FIG. 1, the medical service kiosk 100 and medical facility 202 communicate with the cloud services system 300 via a wired, wireless, or internet connection network 200. The medical service kiosk 100 gives access to at least one patient to a secure medical session with a physician or healthcare professional that is located at the remote medical facility 202, or on a remote electronic device 204 at a remote location, such as their office, home, or an alternative remote location over the network terminal 200. Patient access to the medical session with a physician at a medical facility 202 hosted by the cloud services system 300, is accomplished by use of an electronic device including any of, but not limited to, a tablet, laptop or notebook computer, or a desktop computer. It is appreciated that each medical session may be recorded and stored in memory or a database 308 provided by the cloud services system 300 for later viewing. In application, each electronic device includes the necessary electronic components required to communicate with the medical facility 202, and cloud services system 300. As such, each patient electronic device may include audio and video circuitry, a keyboard or touchpad, memory or access to memory, one or more processors, I/O network interface, application program interface, read/write memory (RAM), read-only memory (ROM), and a visual screen or display for navigating through a medical session hosted on the cloud services system 300.

Each electronic device utilized to connect to the cloud services system 300, hosting the medical session, electrically communicates via a wired (land line), wireless, or internet network including VOIP (voice over internet protocol) network. The communication network 200 may include wireless communication including but not limited to: WLAN (wireless local area network, Wi-Fi (IEEE 802.11), WPANS (wireless personal area networks, such as Bluetooth (IEEE 802.15), Infrared, ZigBee), WMAN (wireless metropolitan area network, such as WiMax (IEEE 802.16)), WWAN (wireless wide area networks, internet), and GAN (global area network), a mobile wireless communication system, such as 3G, 4G, or 5G, an internet-protocol based communication system. The communication network 200 may include a wired communication including but not limited to, fiber optic systems, a telephone network such as a PSTN (public standard telephone network). The communication network 200 may further include a radio frequency network (RF), a cable network, a satellite network, and an internet or intranet network, where each network is adapted for transmitting, and receiving data, information, audio, video, texts, messages, emails, and files between the medical kiosk electronic devices and the medical facility 202, and cloud services system 300. It will be noted that network, interface, communication and information exchange equipment, components or peripherals may be employed, including, but not limited to, use of base stations, servers, routers, switches, repeaters, towers, antennas, Ethernet hubs, wired or wireless data path ways, modems, virtual private networks (VPN), modems, proxy servers, application program interfaces (APIs), networking adapters, or gateways. Encryption protocols may also be employed to secure the transmitted information, data, or messages. For example, a few exemplary forms of encryption include IPsec, or secure sockets layer (SSL), and symmetric or asymmetric encryption.

The cloud service system 300 comprises an internet based computing service system including in one embodiment, a user registration/authentication server 302, a web platform server 304, and an administrative server 306, all networked together by way of a central database 308, and computing system 310. The cloud service system 300 may include a public, private, or hybrid cloud configuration based on various cloud service models including any of an Iaas (Infrastructure as a Service), PaaS (Platform as a Service), or Saas (Software as a Service) model. The type of cloud configuration implemented is based on need for data security, control over the infrastructure, sensitivity of data and applications, and industry regulations or standards. In a preferred embodiment, the cloud computing services 300 comprises the Amazon Web Services (AWS) elastic compute cloud EC2 architecture that supports simple email service (SES), and simple notification service (SNS) to allow both email and short message service (SMS) communication between patients/medical care providers, and the AWS cloud computing services 300, via, electronic devices over network 200. The AWS cloud computing services 300 also supports simple storage service (a single web-services interface) to store and retrieve data from anywhere on the web.

With continued reference to FIG. 1, after establishing a secure connection with a health care professional over the communication network 200, which will be described further herein below, the patient will be able to communicate with the healthcare professional (e.g., clinician, physician, pharmacist, nurse practitioner, nurse, nursing assistant, etc.) and provide the healthcare professional with medical information through the use of equipment that is provided inside of the patient station 102 and is connected to the electronic device inside of the medical service kiosk 100. The health care professional or physician will be able to guide and instruct the patient on how to use the equipment provided therein. The equipment inside of the patient station is communicable with the central processor of the electronic device inside of the patient station, and can transfer readable data to the cloud services system 300, and the network terminal accessible 208 or electronic device 204 being used by the physician overseeing the medical session. The physician may review the information (i.e., readable data) that is being transmitted in real-time, and render a medical opinion. The health care professional will also be able to provide medicine that can be dispensed by the medical kiosk medical storage space provided by the medical services kiosk 100, or, alternatively, remotely print a prescription or send a prescription notification to a nearby pharmacy for pick-up. In one exemplary form, the medical services kiosk 100 may be connected to a back-up generator or to at least one uninterruptible power supply (UPS) battery that is powerful enough to energize the medical services kiosk, and particularly the equipment inside of each respective patient station in the event of an unexpected power loss.

Figure 2:
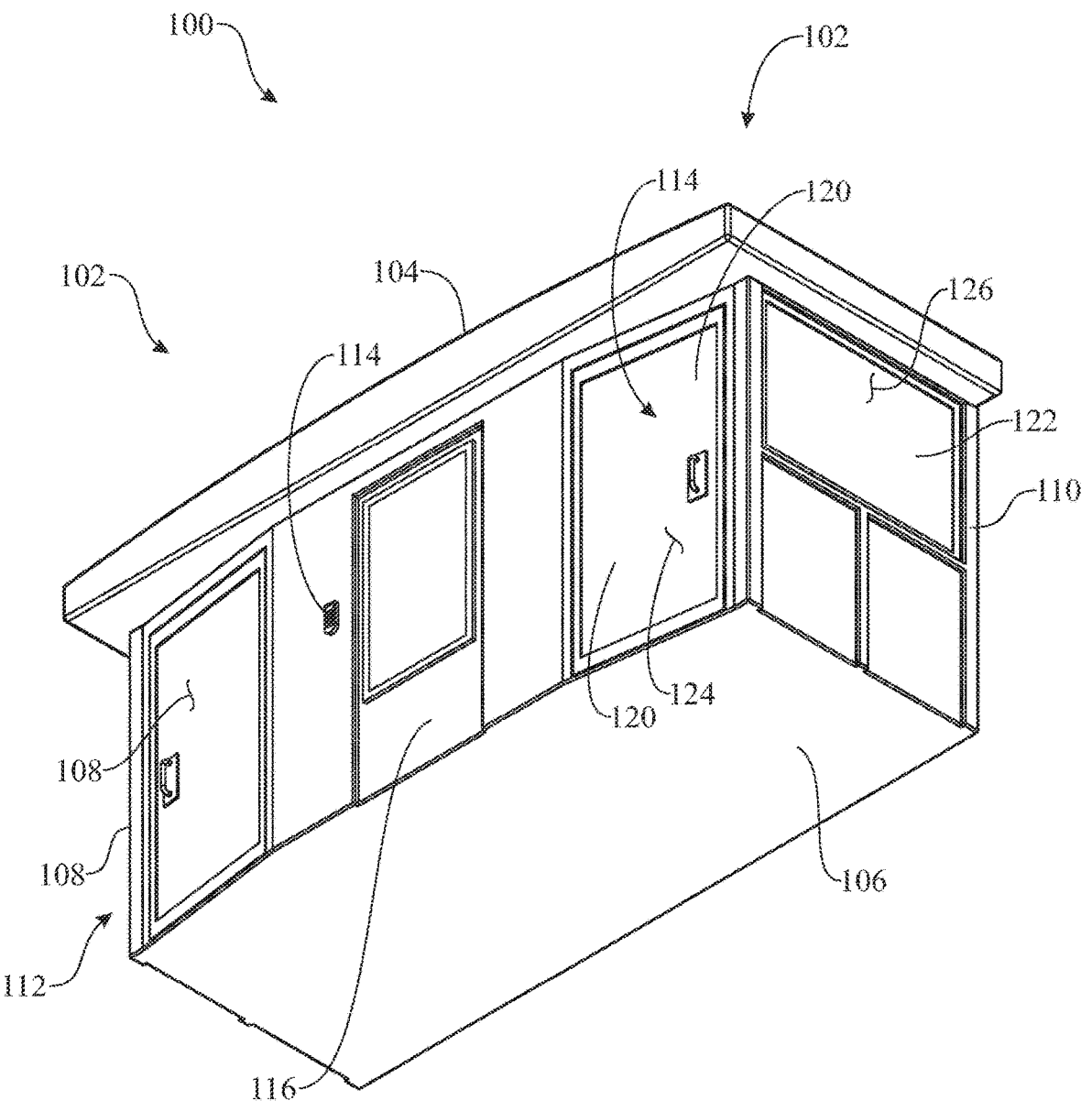
FIG. 2 presents a bottom isometric view of an exemplary
embodiment of a medical service kiosk.
Figure 3:
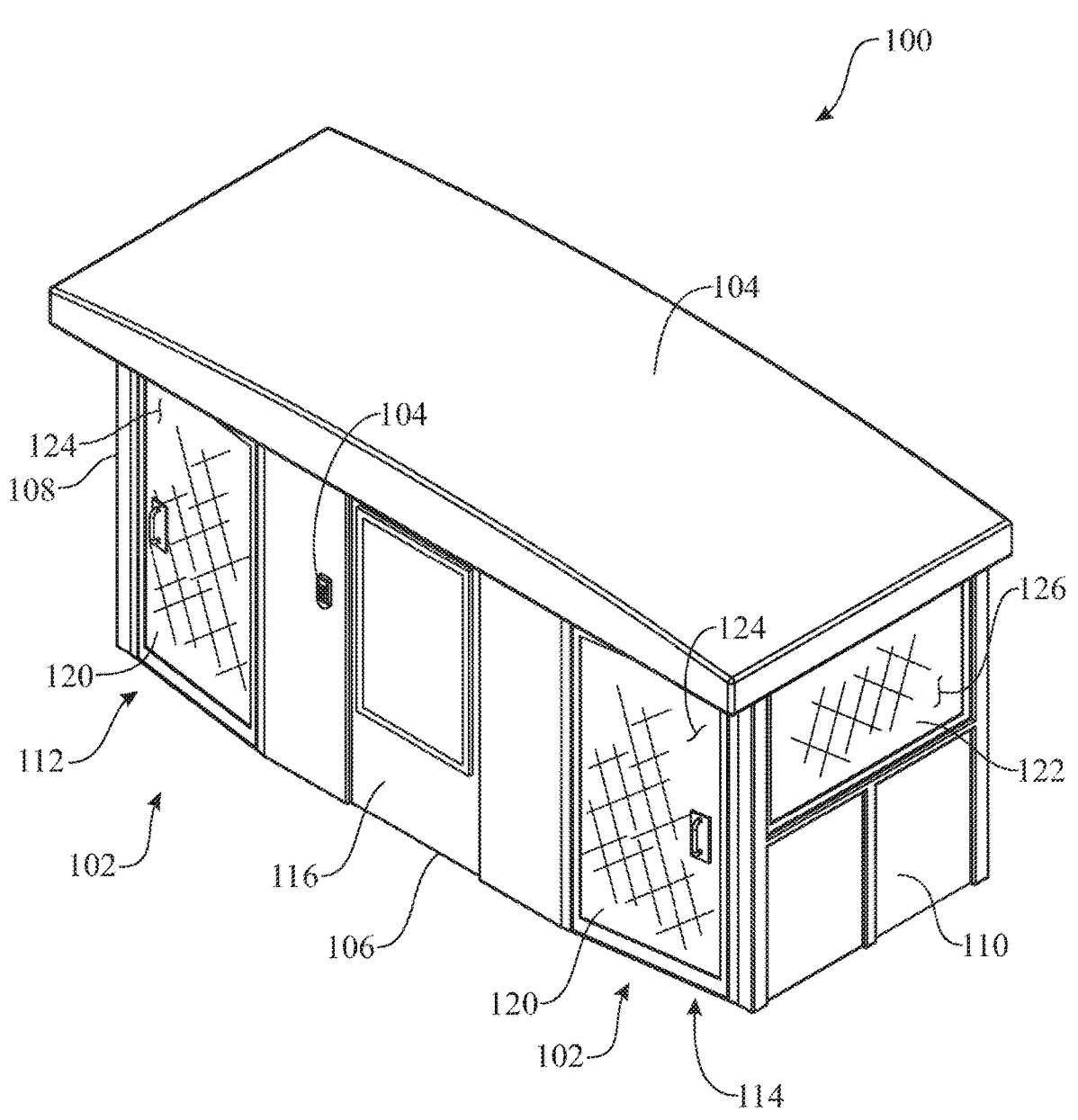
FIG. 3 presents a top isometric view of the medical
service kiosk originally shown in FIG. 2, wherein the
window and door panels include an automatic glass shading
element that provides privacy to a patient when using the
medical service kiosk.
Figure 4:
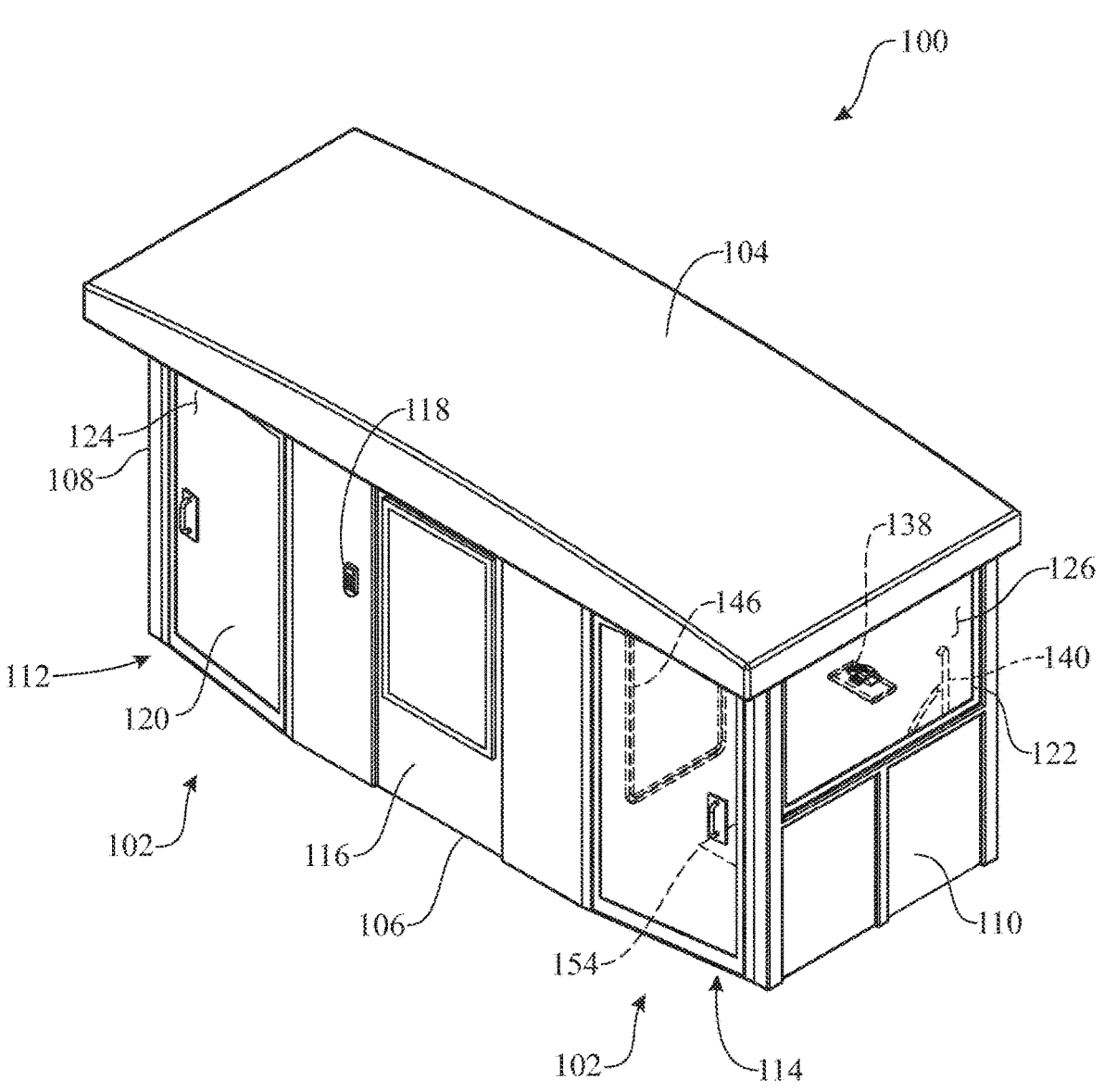
FIG. 4 presents a top isometric view of the medical
service kiosk originally shown in FIG. 2, with the automatic
glass shading element turned off and showing the interior of
the patient station.

Referring now to FIGS. 2-4, the medical services kiosk 100 is illustrated in accordance with one exemplary embodiment of the present invention. The medical services kiosk 100 includes a closed top 104, a closed bottom 106, and opposite left 108 and right 110 sides. In this particular example, as mentioned heretofore, the medical kiosk 100 includes two patient stations 102, a leftmost patient station 112 and a rightmost patient station 114. It should be readily understood, however, that each medical services kiosk 100 may include at least one or more patient stations 102. Each medical services kiosk 100 may also include a medical inventory storage vault or space 116. The medical inventory storage space 116 may generally comprise a medical dispenser containing a plurality of medications securely locked therein and/or include medical equipment (e.g., over-the-counter blood pressure equipment, pregnancy tests, blood sugar monitors, etc.) that may be distributed to a patient upon a set of instructions and commands provided over the network by the medical professional (i.e., a physician) that is administering the exam remotely. The storage space 116 may be configured to include a security check device 118 that scans barcodes, RFID, prescriptions, and/or the like, before administering or giving access to the medication and equipment stored therein.

As specifically shown in FIGS. 3 and 4, the leftmost patient station 112 and rightmost patient station 114 each include an entrance door 120 and a side window panel 122 that may include a privacy feature governed by a privacy system. For instance, in one exemplary form, entrance door 120 and side window panel 122 may each be configured to include a privacy glass 124, 126 that includes polymer dispersed liquid crystals whose light scattering power is adjustable through the application of an electrical field. In their natural (i.e., uncharged) state, the liquid crystal molecules are randomly scattered providing an opaque condition that prevents anyone from peering through the glass 124, 126, giving the patient complete privacy (FIG. 3). When a current is applied (i.e., charged state), however, the molecules align to provide a see through condition, as shown in FIG. 4. It is also appreciated that the patient kiosk includes a display device projectable on the privacy glass of the entrance door that notifies other patient's outside of the interior chamber that the patient station is in use.

Figure 5:
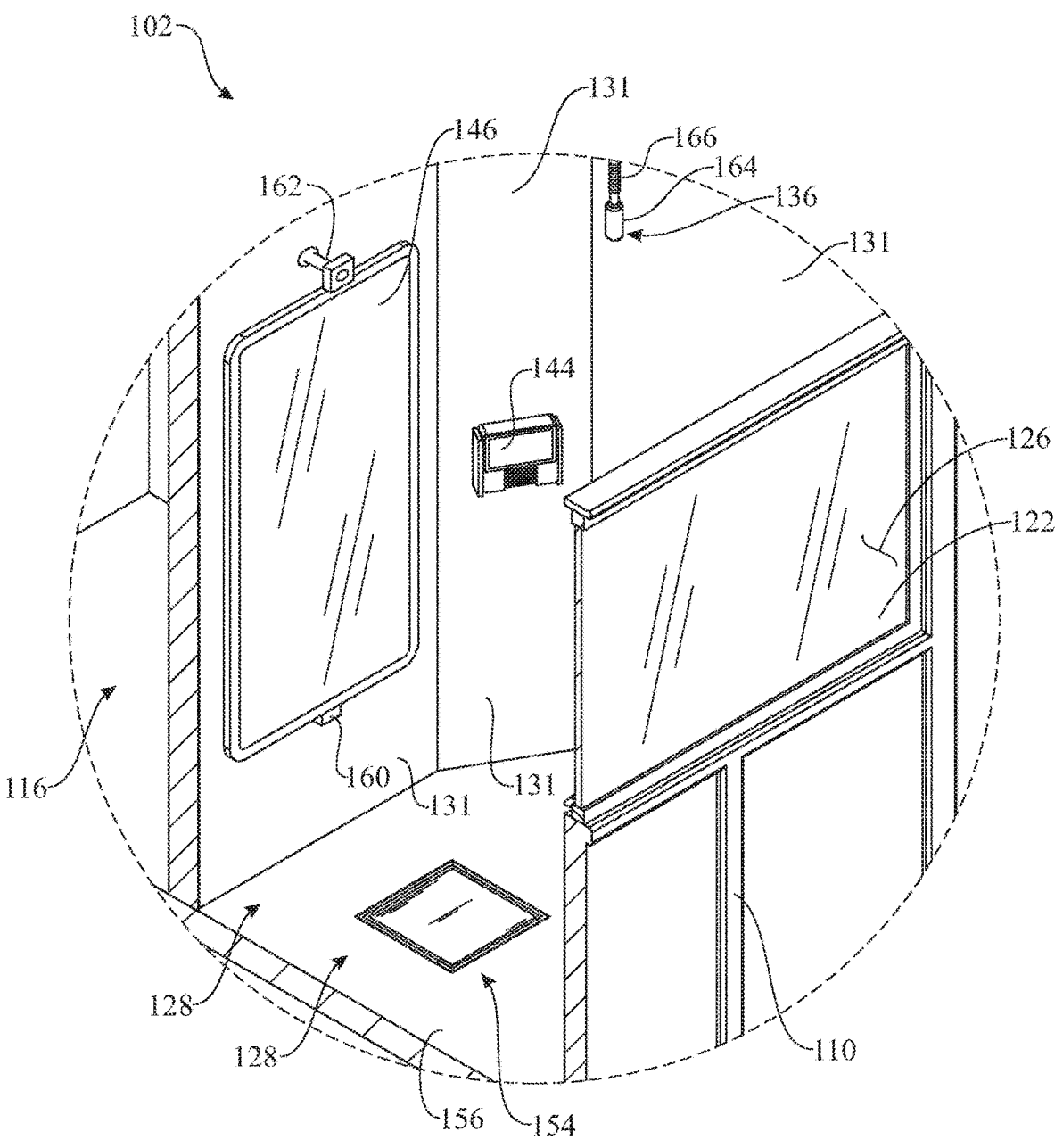
Figure 6:
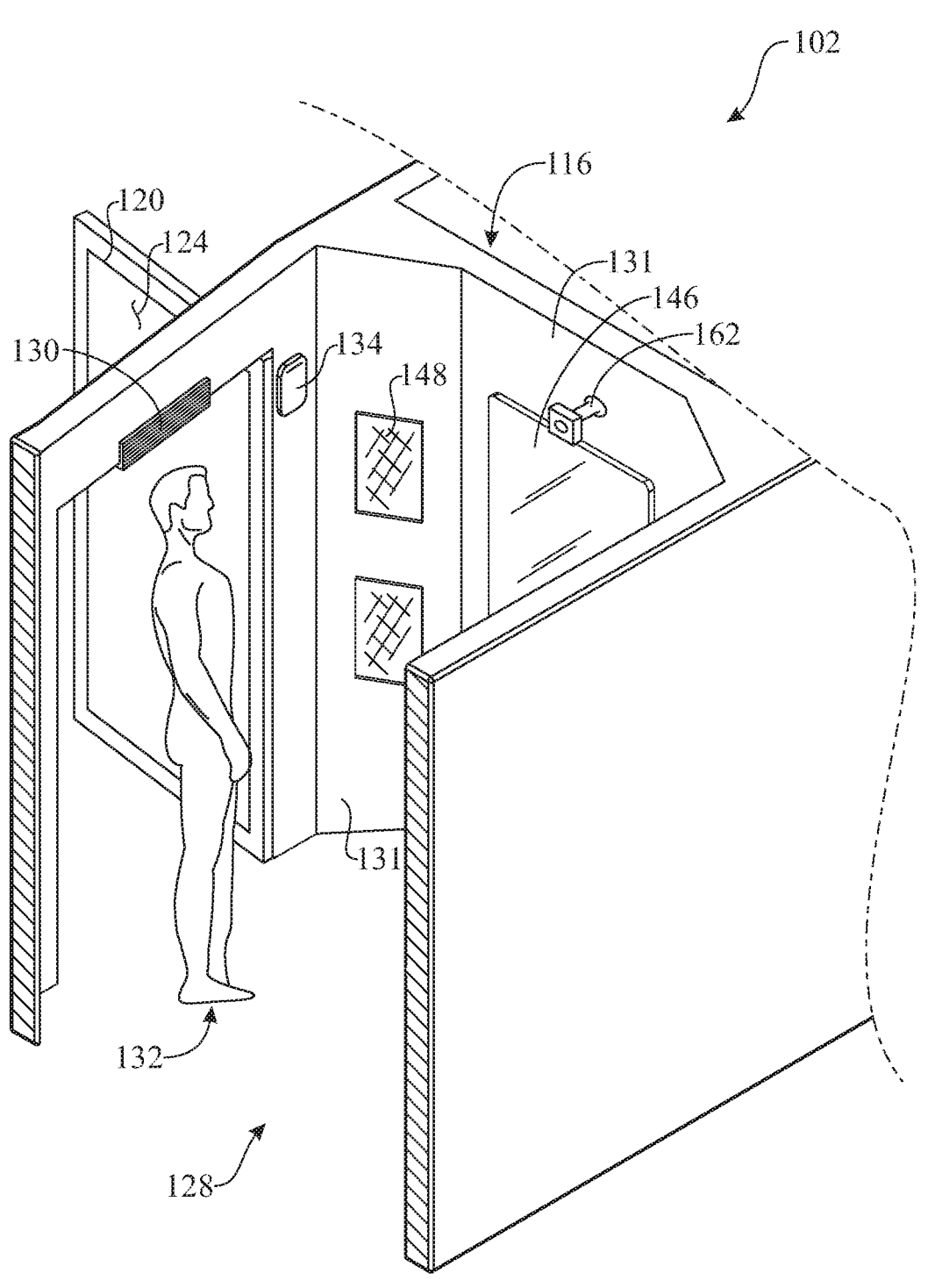
FIG. 6 presents another cut-out view of the medical
service kiosk, showing a patient walking in to the patient
station.

Turning now to FIGS. 4-6, as previously mentioned the medical service kiosk 100 may include more than one patient station 102. Although each patient station 102 may be provided to include certain medical equipment that another station may omit, a vast majority of patient stations 102 are contemplated to be made of a similar shape, size, and be equally equipped to provide a sense of familiarity to the visiting patient regardless of the location of the medical service kiosk being visited. Therefore, the following is a continued description of one exemplary patient station 102.

As is best seen in FIGS. 5 and 6, the patient station 102 generally includes an interior chamber 128 comprising a plurality of walls 131 that are sound proof. The patient station 102 may also include the aforementioned doorway or entrance door 120, which may include an automatic locking mechanism 130. The locking mechanism 130 is contemplated to be part of the privacy system that includes the aforementioned privacy feature on the glass 124, 126 of the entrance door 120 and window panel 122, which can be selectively switched from a see-through condition to an opaque condition and vice versa. It is appreciated that the privacy system be controlled by a power distribution unit (PDU) or control box 134, which may be located in the storage vault 116. The control box 134 in one exemplary embodiment is communicable with the electronic network 200, medical facility 202 and cloud service system 300 and hosts an executable set of instructions or commands. The control box 134, which is isolated from the patient station's electronic device centralized processor, may be connected to a network switch and may receive control commands that the station's centralized processor doesn't. Some control commands may be sent (i.e., executed) by the physician overseeing the medical session, or programmed to run automatically by pre-set programmed protocols. In one exemplary embodiment, control box 134 may be configured to automatically activate the privacy system after a patient 132 has initiated their session. For instance, after a patient 132 has walked into the interior chamber 128 of the patient station 102 and has successfully initiated their medical session as will be described herein below, the privacy system activates prompting the automatic locking mechanism 130 to engage and secure entrance door 120 to prevent entry into the patient station 102. At the same time, the privacy system activates the privacy feature on the entrance door's glass 124 and window glass 126 to prevent or obscure a sight line view into the interior chamber 128 of the patient station 102. Once the medical session is complete (i.e., the session has been terminated), the privacy system disengages deactivating the privacy feature on the door glass 124, window panel glass 126, and locking mechanism 130 to unlock the door 120. In one exemplary form, the automatic locking mechanism may be provided in the form of an electronic maglock. Alternative locking mechanisms, such as standard door locks, deadbolts, or other types electronic locks that are electronically communicable with an electronic device may be used. The activation and deactivation of the privacy system as described hereinabove, may be operated through firmware and software. It is also contemplated that the physician overseeing the medical session may have control over the activation and deactivation of the privacy system remotely through the terminal being used for the medical session.

Figure 7:
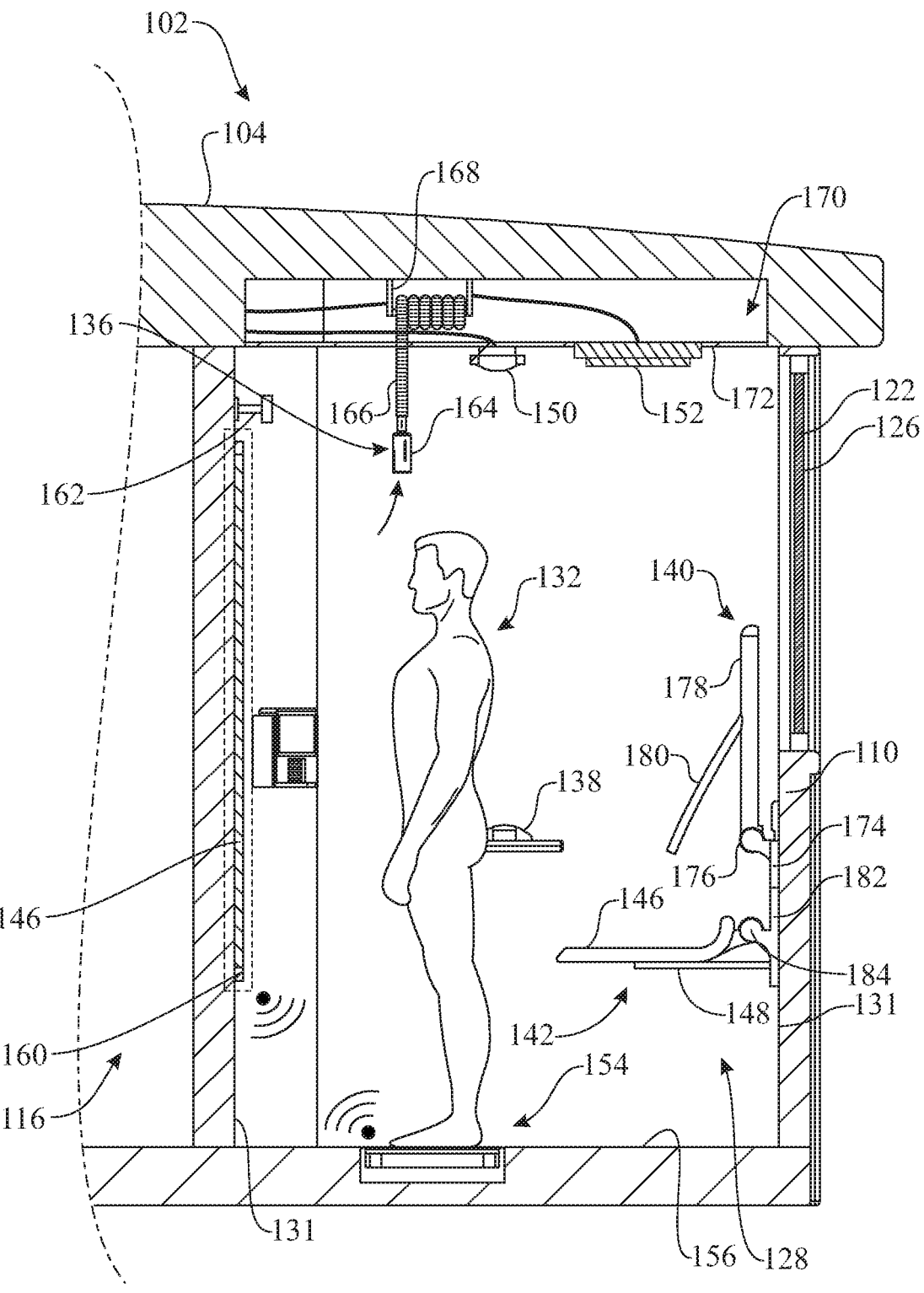
FIG. 7 presents a cross-sectional side elevation view of
the medical service kiosk shown in FIG. 2, with the patient
communicating with a physician before starting a physical
examination.

Referring now to FIGS. 5-7 and 9, the patient station 102 may also include a number of medical and non-medical equipment. For example, as best shown in FIG. 7, the patient station 102 may include a retractable diagnostic camera device 136, a web camera or live-video capturing camera 162 positioned at a wall 131 above a visual device (e.g., a screen) pointing in the general direction of a space that is to be occupied by the standing patient 132. The capturing camera 162 is able to transmit an image of the patient 132 occupying the patient station 102 to the physician 202 conducting the exam at the medical facility 202 (or to the physician on their electronic device 204 shown in FIG. 1). All cameras included in the patient station are communicable and connected to the user interactive display via a wired (e.g., USB connector) or wireless connection (e.g., Bluetooth, internet connection, radio wave frequency, etc.). Each patient station may also include a stethoscope that can be deployed and retracted in a similar fashion to the retractable diagnostic camera, and be mounted to either the ceiling or wall of the interior chamber.

The patient station 102 may also include a biometrical/vitals measuring device 138, an arm support mechanism 140, a seating mechanism 142, a documentation receiving device 144 (or card reader), the user interactive display terminal 146, which is the station's electronic device, may include speakers 148, a microphone 160, a monitor, screen, or projector. The patient station 102 may also include a purification device or ultra-violet sanitation system 150, an interior lighting mechanism 152, and an integrated scaling mechanism 154 comprising an outer flooring 156 and a platform or interior flooring 158. The interior chamber 128 may further comprise a plurality of stationary and retractable sensors, cameras, and other devices that are communicable over a wired and/or wireless network with the station's centralized processor. As illustrated best in FIG. 9, the retractable diagnostic camera device 136 may comprise a camera head 164 that may be configured to include means for measuring and receiving bodily conditions, as well as capturing images. For example, the diagnostic camera device 136 may include an interchangeable camera head 164 to include, but not limited to, a manual focusing head, an otoscope head, a tongue depressor attachment and derm hood head. The camera head may also include buttons that allow the patient to capture images upon the request of the physician overseeing the medical session. A separate camera may also be included to provide thermal images, thermal temperature readings, and color-coded imaging to the physician administering the remote medical session.

The position of the diagnostic camera device 136 may generally comprise a camera head 164 affixed to a camera cord 166 that is set about a linear mechanism 168. As is best illustrated, the linear mechanism 168 may be suspended inside of a cavity 170 provided by a false ceiling 172 inside of the interior chamber 128 of the patient station 102, or alternatively be positioned inside of the medical inventory storage space 116 of the patient station 102 (not shown). It is appreciated that the retractable camera device 136 be arranged or otherwise positioned at a top of the interior chamber 112, generally over a space that is to be occupied by the standing patient 132 and at a height that is easily accessible by the patient 132. In an alternative embodiment, the camera 164, camera cord 166, and linear mechanism 168 may be disposed about a wall surface 131 at a height that is equally accessible by the patient 132.

Figure 10:
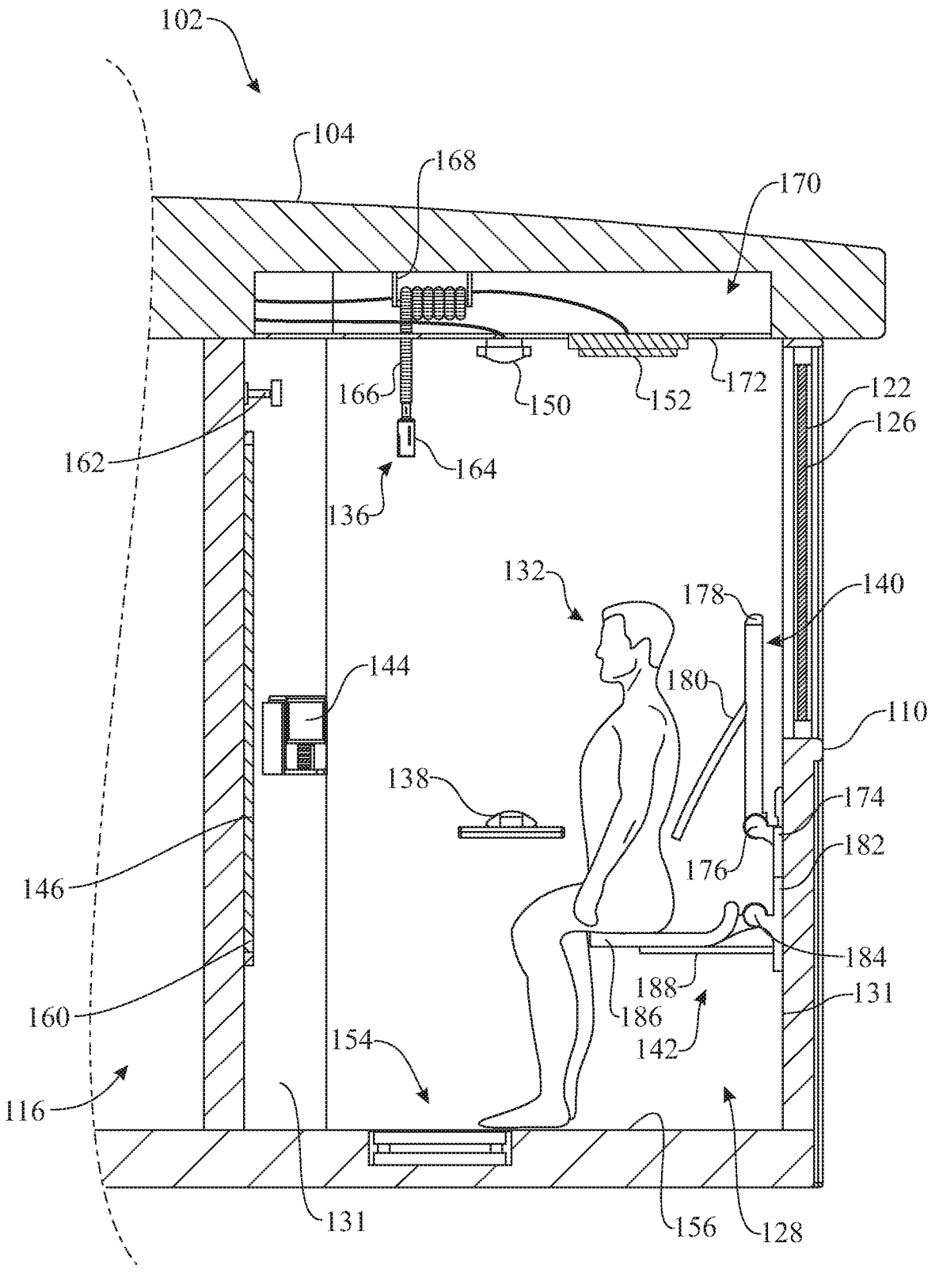
FIG. 10 presents a cross-sectional side elevation view of
the medical service kiosk shown in FIG. 2, illustrating the
patient sitting down talking with a physician on the inter-
active panel.
Figure 11:
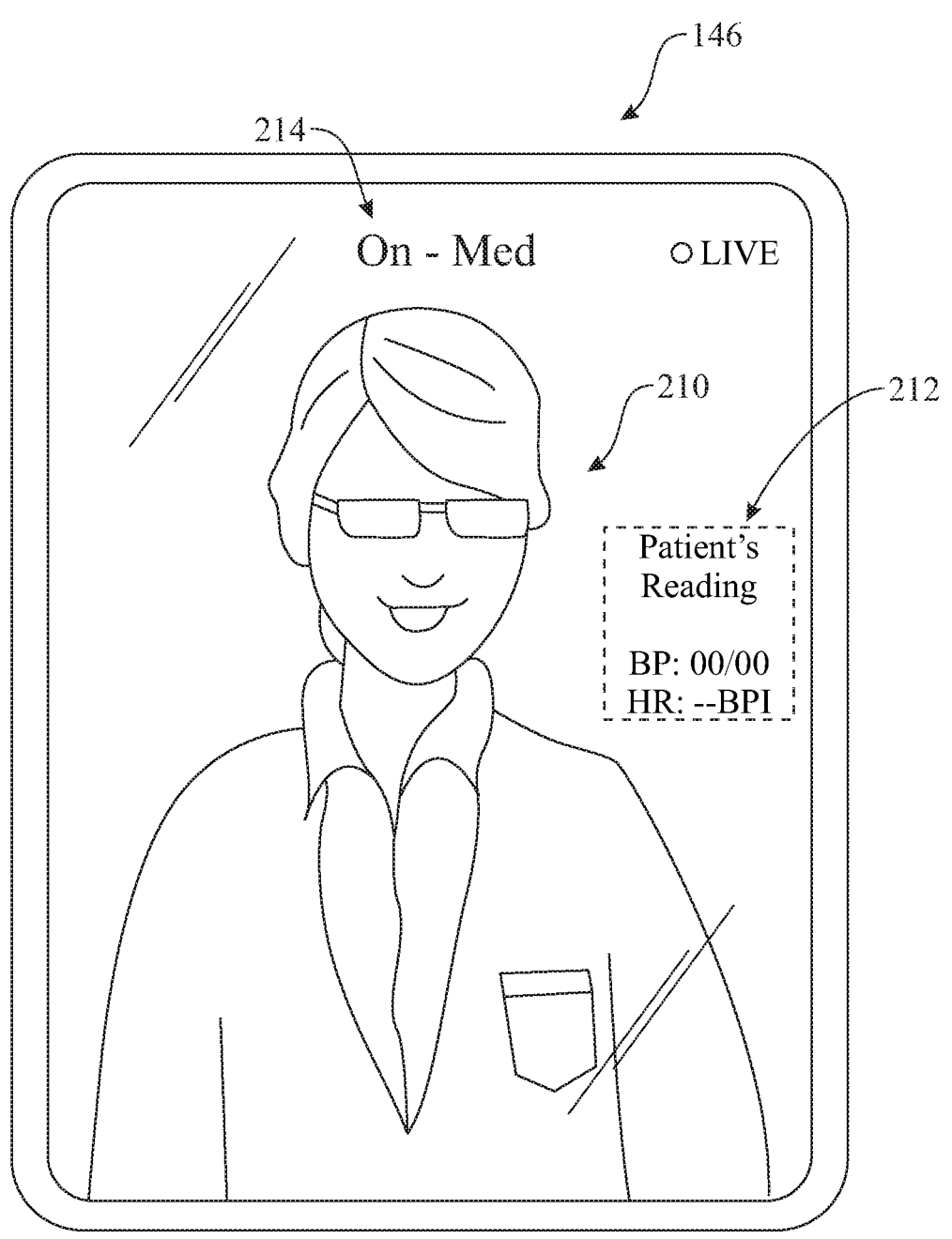
FIG. 11 presents one exemplary embodiment of how a
physician would appear on the interactive panel included in
the patient station.

Turning to FIGS. 7 and 11, each patient station 102 may include a user interactive display terminal 146 that is to be mounted on a wall surface 131 inside of the chamber 128 generally positioned below the capturing camera 162. The user interactive display terminal 146 includes a centralized processor communicable with the internal medical and non-medical equipment inside of the patient station (e.g., camera, diagnostic camera, biometric devices, medical storage unit, printer, etc.), and provides the means for a secure connection with the network 200, medical facility terminal 208, and cloud based system 300 hosting the medical session. The user interactive display terminal 146 is suitable for projecting (or displaying) a real-time image of the physician 210 (or medical professional) administering the exam remotely. As is clearly seen in FIG. 10, it is appreciated that the physician 210 be displayed to the patient 132 in such a way that the patient 132 receives the visual sensation that the physician 210 is virtually present in the room. It is also appreciated that the display of the user interactive display terminal 146 be configured to be adjusted manually or automatically to the height or preference of the patient 132, so that the physician 210 or health care professional performing the remote exam can see the patient 132 and what they are doing at all times. The medical services kiosk 100 is technologically equipped to the extent that the patient 132 is constantly receiving a live image of the physician 210 administering the exam, with the physician 210 having the ability to display on the screen (of the user interactive display terminal 146) any medical readings that are pertinent to the discussion of the diagnosis of the patient 132. For example, as shown and illustrated in FIG. 11, the physician 210 may be speaking to the patient while deciding to display a picture in picture (PIP) 212 at a respective visual corner on the display device of the user interactive display terminal 146 of the patient's 132 vital readings, sugar levels, blood levels, etc. The simulated screen image may also be configured to include a background image being displayed behind the physician 202 that may include, but is not limited to, the logo 214 or other indicator associated with the remote medical facility, physician, and/or insurance company covering the patient 132.

Figure 12:
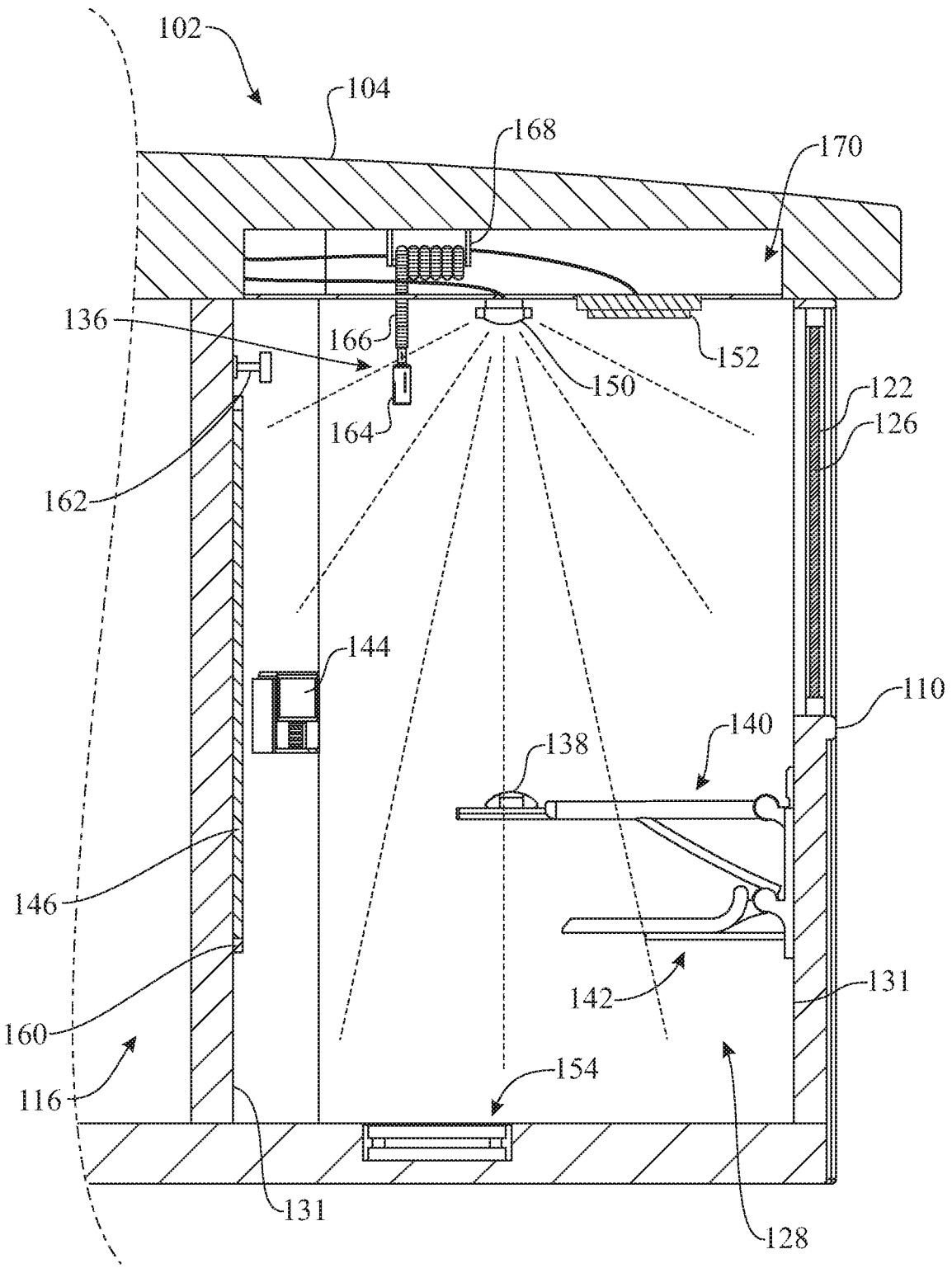
FIG. 12 presents a cross-sectional side elevation view of
the medical service kiosk shown in FIG. 2, showing a
cleaning mechanism being used to sanitize the room once
the patient has left the patient station.

Returning to FIGS. 7, 9 and 10, the arm support mechanism 140 of the patient station 102 may comprise a wall mount 174 having a hinge connection 176 that is removably attachable to an arm rest 178 that includes a support arm 180. As illustrated, the wall mount 174 may be affixed to a wall surface 131, such that the arm rest 178 and support arm 180 can pivot about hinge 176 and be movable between an upward position (shown in FIG. 7) and downward position (shown in FIG. 12). The arm support mechanism 140 may be utilized to provide the patient 132 with an arm stabilizing platform that is necessary when performing certain diagnostic tests. For instance, when a physician 210 requests that the patient 132 take a blood pressure measurement, it is generally known that the arm placement of the patient must be in a bent position and remain still while the test is being performed. In that particular case, the patient 132 may decide to move the arm rest mechanism 140 from the upward position to the downward position and use the arm mechanism's arm rest 178 as a stabilizing platform to perform the test. Likewise, the arm support mechanism may be utilized for alternative tests that require the stabilization of the patient's arm (e.g., blood work, pulse and oxygen readings, etc.)

Figure 8:
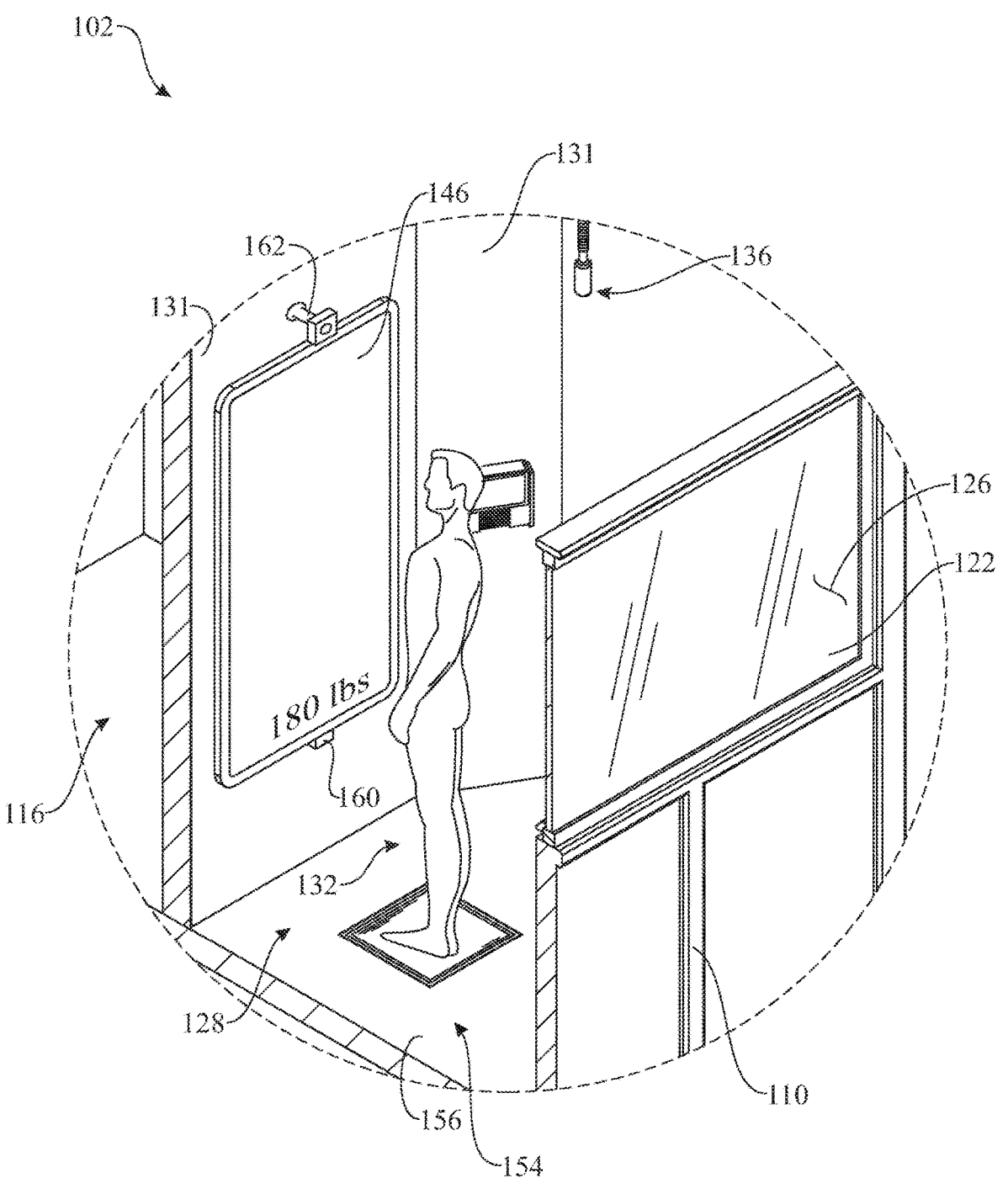
FIG. 8 presents a presents a cut-out view of the medical
service kiosk shown in FIG. 2, illustrating a patient standing
on top of a scale mechanism that's incorporated into the
flooring system.
Figure 9:
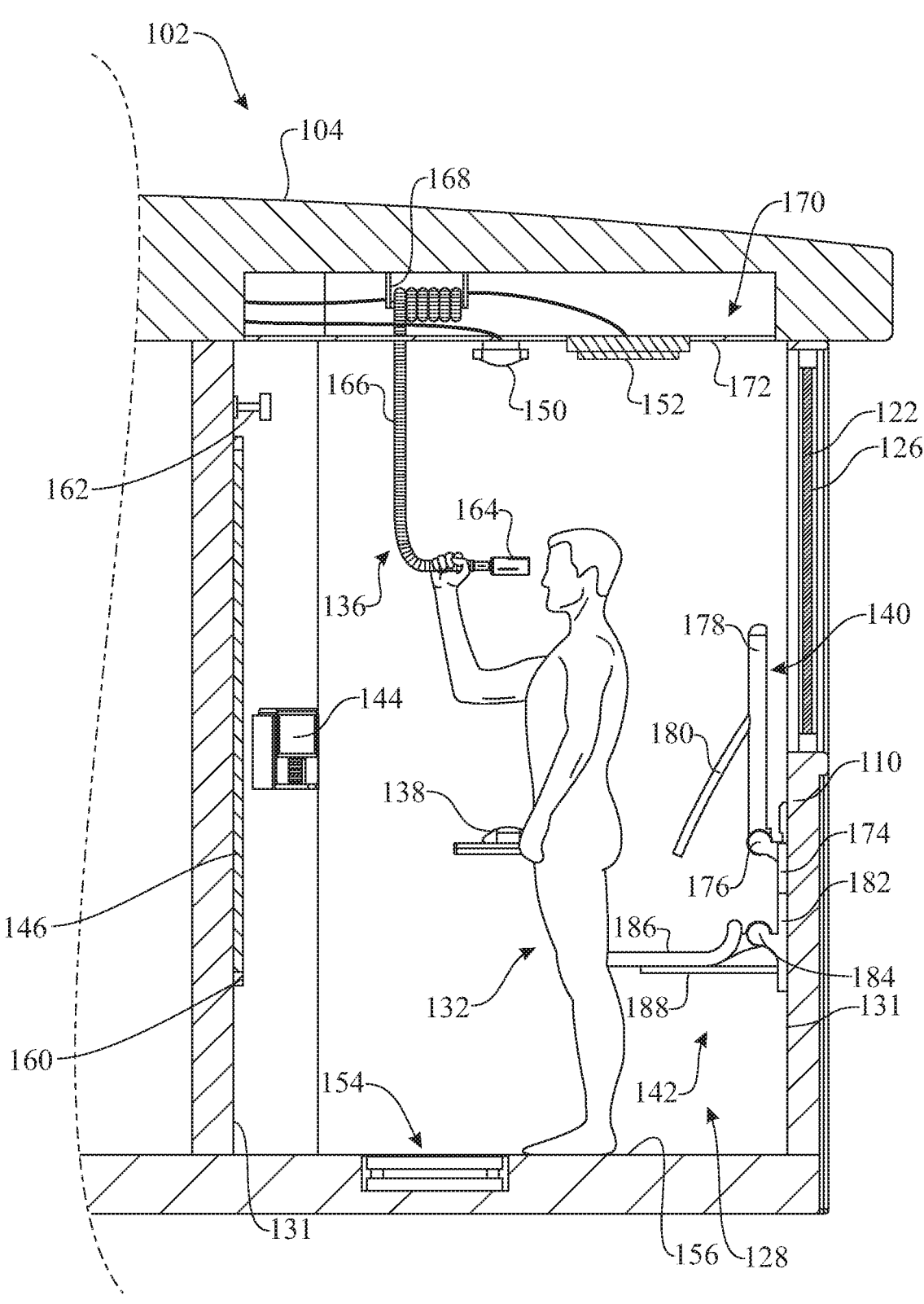
FIG. 9 presents a cross-sectional side elevation view of
the medical service kiosk shown in FIG. 2, illustrating the
use of the medical camera device included in each patient
station.

Continuing with FIGS. 8 and 9, the seating mechanism 142 of the patient station 102 may generally comprise a wall mount 182 that includes a hinge connection 184, a seat 186, and a support member 188. In one exemplary form, wall mount 182 may be attached to a wall surface 131 proximate to the arm mechanism 140. Seat 186 may then be hingeably attached to hinge 184. The seat mechanism 142 is movable between an upward position (not shown) and a downward position (shown in FIG. 7), and is designed to withstand a heavy load of about 500 pounds. The seating mechanism 142 is contemplated to be positioned below and to a side of the arm support mechanism 140 that was described herein above. The relative position of the seat mechanism 140 and arm mechanism 140 is one that simulates a chair with an arm rest provided at an adequate height. Both the arm mechanism and seat mechanism may be height adjustable to account for patients of different sizes.

The operational use of the medical services kiosk, and more particularly, the patient station 102 that is provided in each medical service kiosk is now discussed with reference to FIGS. 1, and 6-12.

In operation, the patient 132 enters into one of the separated (i.e., private) interior chambers 128 of the patient station 102 through the entrance door 120. The patient 132 may then be able to initiate a session by interacting with the documentation receiving device 144 or user interactive display terminal 146. In one exemplary form, the initiation process may include the patient 132 entering a patient station 102 and interacting with the documentation receiving device 144 that is contemplated to be positioned at an opposite side of the patient station's entrance door 120. The documentation receiving device 144 may include a processing unit that is able to communicate with the centralized processing unit of the user interactive display terminal 146 that is communicable over the network 304 with the cloud based service 300 that is to host the medical session (FIG. 1). The patient 132 may initiate the session by providing payment or insurance information in the form of a card that is readable by the documentation receiving device 144 or providing information prompted by the user interactive display terminal 146 upon entry of the patient station 102. Once payment or the requirement to input information has been satisfied, the cloud based system 300 which is linked and communicates with the electronic device (i.e., terminal display 146) of the patient station begins the process of establishing a medical session with an available healthcare professional. The system begins by doing a search query to see which health care professional accessing a terminal 208 at a medical facility (or an electronic device 204 elsewhere) is available for a match. The process of facilitating or hosting a medical session executed by the cloud based system 300 may be carried out by a tangible computer-readable storage medium that holds machine-readable instructions executable by a logic machine (i.e. one or more processors or programmable control devices) to provide, implement, perform, and/or enact the described methods, processes and/or tasks. When such methods and processes are implemented, the state of the storage machine may be changed to hold different data. For example, the storage machine may include memory devices such as internal or external hard disk drives, CD, or DVD devices. The logic machine may execute machine-readable instructions via one or more physical information and/or logic processing devices. The logic machine may be configured to execute instructions to perform tasks for a computer program, and/or may include one or more processors to execute the machine-readable instructions. The computing system may include a display subsystem to display an application interface, or graphical user interface (GUI), or any visual element of the methods or processes described above.

To provide and ensure a secure, user-authorized access to a session, the physician or health care professional must go through an authentication process provided by the authentication server 302, which may include a software-based, and/or hardware-based authentication device, systems, or methods. Authentication may comprise a single-tier, two-tier, or multi-tier authentication protocol process. Examples of authentication protocols may include, but are not limited to, smart card technology, browser or digital certificates, hardware OTP tokens, software tokens, hardware security modules (HSM), or biometric authentication using one or more sensors for sensing fingerprints, hand geometry, iris or retinal patterns, or voice sampling or recognition. Other authentication protocols may include, IP security (IPSec) authentication methods, including the Kerberos protocol, private or public key certificates, or a simple pre-shared secret key, Challenge Handshake Authentication Protocol (CHAP), or the Extensible Authentication Protocol (EAP). Authentication based on single or multiple tier authentication system may include for example, use of a name/ password, setting up answers to challenge questions, setting-up image recognition, or providing numerical or alphabetical information in a captcha text-entry box.

Once a patient has been matched with a physician and a bidirectional connection has been established, the patient 132 may be visually and auditorily prompted with additional introductory questions. For example, the patient 132 may be asked to provide and/or input additional information, such as medical history, if they are under any medications, or additional relevant information. In an alternative example, the information associated with the patient 132 may be linked and integrated from an outside data source by way of logging in to an account, which then may be accessible by both the patient and physician performing the remote medical assessment. As soon as the medical session has been established, the patient station's 102 privacy system 124 may be activated by the physician overseeing the medical session to lock door 130, and activate the privacy features on the glass surfaces 124, 126 of the door 130 and window panel 122 as described herein above. A message may be projected on the glass surface of the entrance door notifying other potential patients that the present patient station is in use.

Referring to FIGS. 7-10, the interior chamber 128 of the patient station 102 is configured for the patient 132 to sit in the patient seating mechanism 142 with their back aligned or supported by a wall surface 131 of the interior chamber 128, and able to use the arm support mechanism 140 provided, if necessary. The patient station 102 of the medical services system 100 may measure the weight of the patient 132 by requesting that the patient utilize the integrated scaling mechanism 154 provided therein, which is best shown in FIG. 8. The scaling mechanism 154 may include a calibrated scale, a plurality of measurement sensors, or any other means suitable for obtaining an accurate weight and/or height of the patient 132, and may be integrated with the remainder of the flooring 156 within the interior chamber 128. For instance, with respect to a height measurement, a height measurement device may be mounted to the ceiling of the interior chamber or a wall surface above a space that is to be occupied by the patient to measure the patient's height. The height measurement device may be connected to the electronic device included with the patient station.

As can be best understood by FIG. 9, the patient 132 is able to provide their biometrics and body vitals by applying, engaging, or otherwise using, the biometric/vitals measuring device(s) 138 provided inside of the patient station 102. In one non-limiting embodiment, the biometric/vitals measuring device 138 may comprise body sensors and blood pressure monitoring technology. The biometric/vial measuring device 138 may also include medical technology suitable for acquiring vital signs of the patient 132, such as, a telemetric monitor, EKG machine, and a pulse oximetry device. In one exemplary form, the biometric/vitals measuring device 138 may include an adjustable bracelet-like mechanism comprising a cavity suited for adjustable fitting to the arm of the patient 132 to obtain the blood pressure reading of the patient. In another example, the biometric/ vital measuring device may include leads that are attachable to the patient to provide telemetry readings readable by the physician. As previously stated heretofore, the equipment inside of the patient station is communicable with the station's electronic device and configured to transfer data that is transferable over the network to the cloud based system 300 and remote network terminal 202 accessible by the physician 210 administering the exam remotely.

Additionally, the patient 132 under the supervision and guidance of a physician 202 may also use the retractable diagnostic camera device 136 suspended above the patient 132 or wall surface 131 to run a series of tests. For example, but not limited to, testing their pupillary light reflex, eyes, cars, both anterior and inferior surfaces of the patients nose, inspect their own mouth for oral mucosa, lesions, moisture cracking, etc. all under the careful guidance and watch of the physician.

As seen in FIG. 8, the head 164 of the retractable diagnostic camera device 136, which may be suspended above the standing patient 132, may be selectively grasped and pulled down by the patient 132. As the head 164 of the diagnostic camera 136 is pulled down, the camera cord 166 wrapped around the linear mechanism 168 suspended above the false ceiling 172 of the interior chamber 128 uncoils, providing the patient with sufficient cord length to easily point the head 164 of the diagnostic camera 136 wherever the patient is requested to do so by the physician administering the remote exam. After the patient 132 is done utilizing the diagnostic camera 136, it is appreciated that the linear mechanism includes a recoiling mechanism that when engaged the linear mechanism 168 recoils the portion of the camera cord 166 that was uncoiled when the patient pulled down the camera, thereby returning the diagnostic camera 136 back to its original position.

In summary, the patient 132 will be able to use the station's equipment to provide the remote examining physician 202 with any necessary data to render a medical diagnosis, or at the very least, allow the physician 202 to rule out medical conditions if a medical diagnosis can't be diagnosed by the physician.

Continuing in FIGS. 10 and 11, as previously stated the patient 132 will be able to have bidirectional communication with the physician 202 by way of the user interactive display terminal 146. The physician will be able to display relevant medical information on the user interaction panel's screen and talk to the patient 132 in real-time. As the session is coming to a close, the physician 202 may be able to dispense medication by way of the medical inventory storage space 116 included in the medical services kiosk 100. Alternatively, if the medication needed is not in-stock (or stored) by the inventory storage space 116, the physician will be able to put in an order remotely for the patient 132 to pick up their prescription at a nearby pharmacy; or print a prescription with by way of a printer that may be stored in the medical inventory storage space 116.

As shown in FIGS. 7, 9, 10 and 12, the privacy chamber or interior chamber 128 of the patient station 102 may include a purification or ultra-violet (UV) sanitation system 150. The ultra-violet sanitation system 150 can be disposed about the false ceiling 172 of the patient station 102. The UV sanitation system is generally controlled and powered by the PDU or control box 134. Similar to the description provided hereinabove with reference to the control box and privacy system, the UV sanitation system is governed by an executable set of instruction or commands provided by the control box 134. The UV sanitation system 150 may be commanded to activate by the physician overseeing the session as soon as the medical session has been terminated and the patient 132 has left the interior chamber 128. In one exemplary form, the physician may make an announcement that can be heard inside of the interior chamber before activating the UV sanitation system 150. Alternatively, the UV sanitation system can be programmed to run on a set schedule. For instance, the system may be programed to run for a pre-set amount of time every time it detects no movement within the chamber every 2 to about 4 hours during the day/night. Movement detection, in one exemplary form, may be verified by personnel viewing images being provided by the camera included in the interior chamber or through a motion sensor. The ultra-violet sanitation system 150 is designed to sterilize or sanitize the interior chamber 128 by neutralizing or killing organic and inorganic matter within the interior chamber 128 by way of ultraviolet lighting when the room is vacant and/or through the use of an ultrasound emitting device that neutralizes or kills organic and inorganic matter through ultrasound waves.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A healthcare station comprising:
   a glass on a door to an interior area of the healthcare station, the glass electronically transitions between one of a non-transparent state or a transparent state;
   a computing device configured to match a patient in the healthcare station with a healthcare professional that is remote, wherein the match triggers a medical session;
   the computing device is configured to trigger a signal that transitions the glass into the non-transparent state and displays a message on the glass that the interior area is occupied according to the match, and the computing device triggers an automatic locking of the door;
   a diagnostic camera that is retractable associated with one of a ceiling or a wall upon which the diagnostic camera retracts, and the diagnostic camera captures visual health data about the patient; and
   a purification system that emits one of an ultraviolet light or an ultrasonic wave upon ending of the medical session, and reception of a signal from a sensor that indicates the interior area is vacant.

2. The healthcare station of claim 1 further comprising:
   an interior display device configured to display an audio-visual prompt with a question, wherein the interior display device is located within the healthcare station and the audiovisual prompt is output subsequent to the match; and
   the computing device is coupled to the interior display device that is configured to receive a response for the audiovisual prompt from the patient.

3. The healthcare station of claim 1 further comprising:
   a scale coupled to a floor of the interior area that is configured to measure a weight of the patient.

4. The healthcare station of claim 1 further comprising:
   an interactive display coupled to the computing device; and
   the computing device is configured to receive one of payment data or insurance data for the medical session from the patient using the interactive display.

5. The healthcare station of claim 1 further comprising:
a vitals acquisition device that is configured to acquire vitals data from the patient within the interior area; and
wherein the vitals acquisition device is one of a biometric device, a telemetric monitor, an electrocardiogram (EKG) device, a pulse oximetry device, or an adjustable bracelet to measure a blood pressure from the patient.

6. The healthcare station of claim 1, wherein the diagnostic camera has a self-recoiling mechanism.

7. The healthcare station of claim 1 further comprising:
a networking device coupled with the computing device that is configured to establish a data link upon the patient logging into an account, and the account having patient information; and
the computing device is configured to access the patient information through the data link.

8. The healthcare station of claim 7 further comprising:
a leftmost area and a rightmost area that receives the patient, and the interior area is located at the rightmost area;
a printer located within the interior area;
the networking device is configured to receive an instruction to issue a prescription from a remote device associated with the healthcare professional; and
the computing device is configured to trigger a signal for the printer to print the prescription.

9. The healthcare station of claim 7 further comprising:
the networking device is configured to receive an instruction to issue a prescription from a remote device, and the remote device is associated with the healthcare professional; and
a dispenser is configured to automatically dispense a medication from a storage vault associated with the prescription.

10. A method comprising:
transitioning a glass on a door to an interior area of a healthcare station electronically between one of a non-transparent or a transparent state;
identifying by a computing device a match between a patient in the healthcare station with a healthcare professional that is remote and triggering a medical session;
triggering by the computing device a signal that transitions the glass into the non-transparent state and displaying a message on the glass that the interior area is occupied according to the match, and triggering an automatic locking of the door;
retracting a diagnostic camera within the healthcare station from one of a ceiling or a wall, and the diagnostic camera captures visual health data about the patient; and
emitting by a purification system one of an ultraviolet light or an ultrasonic wave upon ending of the medical session, and receiving a signal from a sensor that indicates the interior area is vacant.

11. The method of claim 10 further comprising:
displaying by an interior display device an audiovisual prompt with a question, wherein the interior display device is located within the healthcare station and the audiovisual prompt is output subsequent to the match; and
receiving a response for the audiovisual prompt from the patient by the interior display device.

12. The method of claim 10 further comprising:
measuring a weight of the patient by a scale coupled to a floor of the interior area.

13. The method of claim 10 further comprising:
receiving by the computing device one of payment data and insurance data for the medical session from the patient using an interactive display, or the interactive display is coupled to the computing device.

14. The method of claim 10 further comprising:
acquiring by a vitals acquisition device vitals data from the patient within the interior area; and
wherein the vitals acquisition device is one of a biometric device, a telemetric monitor, an electrocardiogram (EKG) device, a pulse oximetry device, or an adjustable bracelet to measure a blood pressure from the patient.

15. The method of claim 10, wherein the diagnostic camera has a self-recoiling mechanism.

16. The method of claim 10 further comprising:
establishing a data link by a networking device upon the patient logging into an account, and the account having patient information, wherein the networking device is coupled with the computing device; and
accessing by the computing device the patient information through the data link.

17. The method of claim 16 further comprising:
receiving by the networking device an instruction to issue a prescription from a remote device associated with the healthcare professional; and
triggering by the computing device a signal for a printer to print the prescription, and the printer is located within the interior area;
wherein the healthcare station has a leftmost area and a rightmost area that receives the patient, and the interior area is located at the rightmost area.

18. The method of claim 16 further comprising:
receiving an instruction by the networking device to issue a prescription from a remote device, and the remote device is associated with the healthcare professional; and
dispensing automatically by a dispenser a medication from a storage vault according to the prescription.

19. A station comprising:
a door to an interior area of the station, the door electronically transitions between one of a non-transparent state or a transparent state;
a computing device configured to match a subject in the station with a health professional that is remote, wherein the match triggers a communication session;
the computing device is configured to trigger a signal that transitions the door into the non-transparent state and displays a message on the door that the interior area is occupied according to the match, and the computing device triggers an automatic locking of the door;
a diagnostic camera that is retractable associated with one of a ceiling or a wall upon which the diagnostic camera retracts; and
a cleaning system that emits one of an ultraviolet light or an ultrasonic wave upon ending of the communication session, and reception of a signal from a sensor that indicates the interior area is vacant.

20. The station of claim 19 further comprising:
an interior display device configured to display an audiovisual prompt with a question, wherein the interior display device is located within the station and the audiovisual prompt is output subsequent to the match; and

the computing device is coupled to the interior display
device and the computing device is configured to
receive a response for the audiovisual prompt from the
subject.

* * * * *